(12) United States Patent
Kyvik et al.

(10) Patent No.: US 8,834,427 B2
(45) Date of Patent: Sep. 16, 2014

(54) SLOTTED CATHETER SECUREMENT DEVICE

(76) Inventors: Kurt Kyvik, Ocala, FL (US); Scott Ryan, Ocala, FL (US); Arthur Parkhurst, Ocala, FL (US)

( * ) Notice: Subject to any disclaimer, the term of this patent is extended or adjusted under 35 U.S.C. 154(b) by 135 days.

(21) Appl. No.: 13/134,498

(22) Filed: Jun. 9, 2011

(65) Prior Publication Data

US 2012/0316504 A1 Dec. 13, 2012

(51) Int. Cl.
*A61M 5/32* (2006.01)
*A61M 25/02* (2006.01)

(52) U.S. Cl.
CPC ....... *A61M 25/02* (2013.01); *A61M 2025/0273* (2013.01); *Y10S 128/06* (2013.01); *Y10S 128/26* (2013.01)
USPC .............. 604/180; 128/DIG. 6; 128/DIG. 26; 604/174

(58) Field of Classification Search
USPC ...... 128/DIG. 6, DIG. 26; 604/174, 175, 177, 604/178, 179, 180
See application file for complete search history.

(56) References Cited

U.S. PATENT DOCUMENTS

| | | | |
|---|---|---|---|
| 3,138,158 A | 6/1964 | Gordon et al. | |
| 4,519,793 A | 5/1985 | Galindo | |
| 4,699,616 A | 10/1987 | Nowak et al. | |
| 4,717,385 A | 1/1988 | Cameron et al. | |
| 4,767,411 A | 8/1988 | Edmunds | |
| 4,874,380 A | 10/1989 | Hesketh | |
| 4,915,694 A | 4/1990 | Yamamoto et al. | |
| 5,224,935 A | 7/1993 | Hollands | |
| 5,232,453 A * | 8/1993 | Plass et al. | 604/180 |
| 5,370,627 A | 12/1994 | Conway | |
| 6,273,873 B1 | 8/2001 | Fleischer | |
| 6,765,122 B1 | 7/2004 | Stout | |
| 6,866,652 B2 | 3/2005 | Bierman | |
| 6,875,200 B1 | 4/2005 | Ajagbe | |
| 7,766,880 B1 | 8/2010 | Spinoza | |

* cited by examiner

*Primary Examiner* — Kevin C Sirmons
*Assistant Examiner* — Shefali Patel
(74) *Attorney, Agent, or Firm* — Thomas C. Saitta

(57) ABSTRACT

A slotted catheter securement device adapted for securing a catheter extending generally perpendicularly from skin of a patient, having a base member and a securing member coplanarly oriented, the securing member being joined to the base member non-coextensively, an interior opening, a slot passing through the base member and the securing member in communication with the interior opening; the securing member having a first bridging member and a second bridging member non-coextensively joined to the base member, a securing adhesive layer positioned on at least one of the first and second bridging members, the first bridging member having an attached end and a free end, the second bridging member having two attached ends, whereby the first and second bridging members fold away from the base member to adhere to each other and to the catheter disposed therebetween.

20 Claims, 3 Drawing Sheets

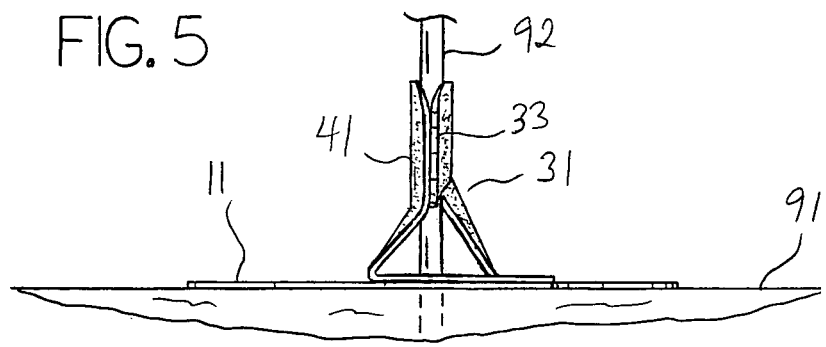
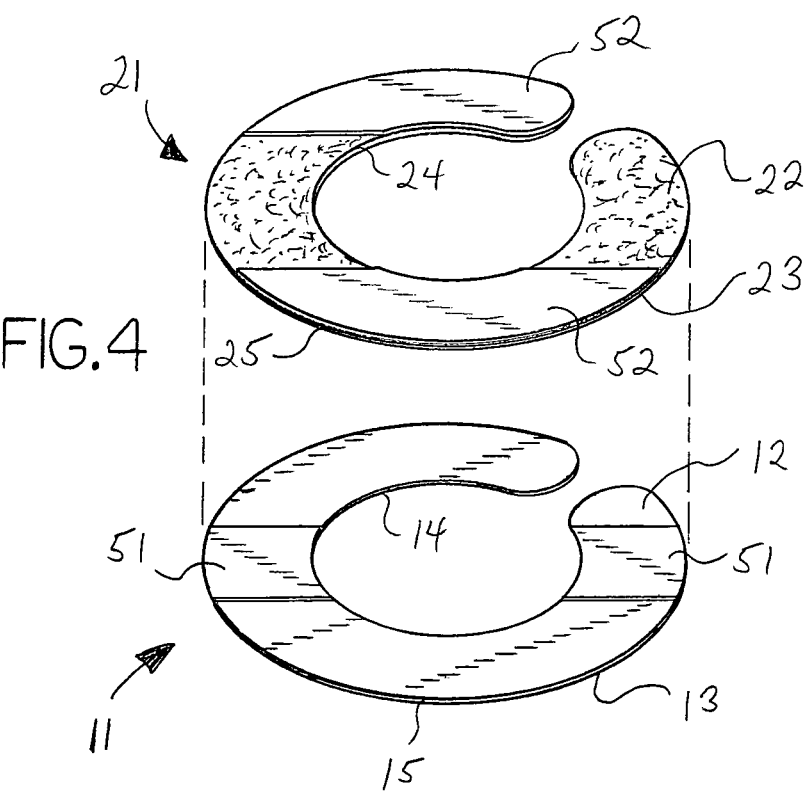

SLOTTED CATHETER SECUREMENT DEVICE

BACKGROUND OF THE INVENTION

This invention relates generally to the field of devices for securing or retaining catheters, IV tubes, drainage tubes or similar medical lines to the skin of a patient at or near the point of insertion, and more particularly relates to such devices securing or retaining catheters and the like that extend generally perpendicularly to the skin surface.

In many circumstances catheters or similar medical lines are inserted percutaneously into the skin of a patient and must remain in place for extended periods of time. To insure that the catheter remains in place, it is known to create frameworks out of strips of adhesive tape to secure the catheter tube to the patient's skin in the proper orientation and to preclude accidental removal. Catheters used with infants are particularly susceptible to accidental dislodgement. In addition to the frameworks created out of strips of adhesive tape by medical staff, dedicated catheter or similar medical line securement devices have been developed for this purpose. Examples of such devices are seen in U.S. Pat. No. 3,138,158 to Gordon et al., U.S. Pat. No. 4,519,793 to Galindo, U.S. Pat. No. 4,699,616 to Nowak et al., U.S. Pat. No. 4,767,411 to Edmunds, U.S. Pat. No. 4,874,380 to Hesketh, U.S. Pat. No. 5,224,935 to Hollands, U.S. Pat. No. 4,915,694 to Yamamoto et al., U.S. Pat. No. 5,232,453 to Plass et al., U.S. Pat. No. 5,370,627 to Conway, and U.S. Pat. No. 6,866,652 to Bierman. Each of these patented devices suffer drawbacks of one form or another, and it is an object of this invention to provide a novel and improved catheter securement device that addresses these drawbacks.

It is an object of this invention to provide a catheter securement device that secures a catheter oriented generally perpendicularly to skin of a patient, wherein the device is quickly and easily applied to or removed from the patient and the catheter.

SUMMARY OF THE INVENTION

The slotted catheter securement device comprises in general a base member adhesively attachable to the skin of a patient and a pair of bridging members connected to the base member whereby the bridging members can be pivoted or folded upward to contact each other, with at least one bridging member being provided with an adhesive capable of adhering to the other bridging member and to the portion of the catheter disposed between the two bridging members. The bridging members are preferably defined as unattached portions of a securing member selectively attached to a portion of the base member, the base member and securing member being composed of sheet material. Preferably the securing member and the base member have matching configurations such that both have an open interior with a slot of greater width than the catheter diameter extending from the interior through the body of the base and securing members. This slotted structure allows the catheter securement device to be positioned or removed with the catheter already in place on the patient.

BRIEF DESCRIPTION OF THE DRAWINGS

FIG. 4 is an expanded view of the embodiment of FIG. 1 showing the base member and securing member.

FIG. 5 is a side view of the embodiment of FIG. 1 showing the bridging members joined to each other and securing a catheter.

DETAILED DESCRIPTION OF THE INVENTION

Figure 1:
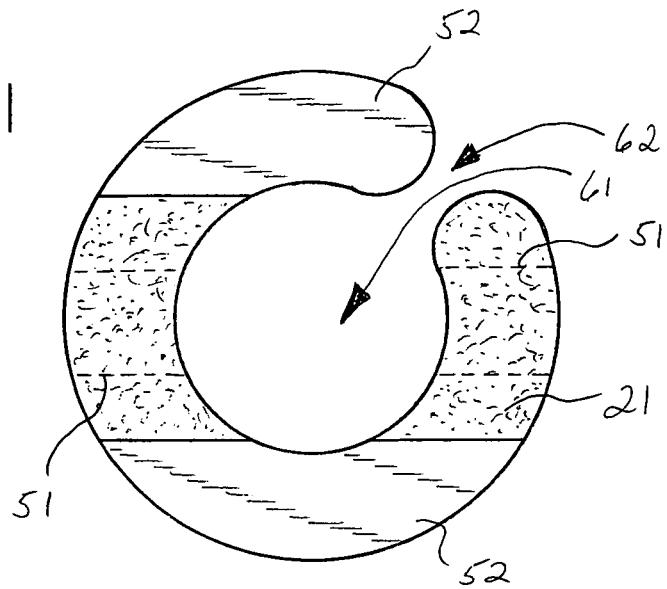
FIG. 1 is a top view of an embodiment of the catheter securement device.
Figure 2:
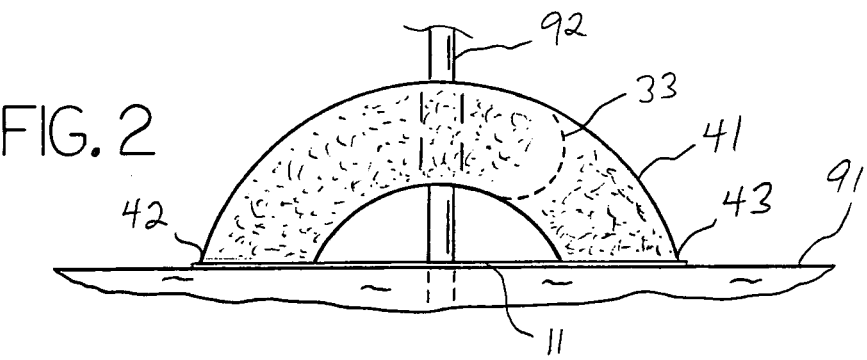
FIG. 2 is a front view of the embodiment of FIG. 1 showing the bridging members joined to each other and securing a catheter.
Figure 3:
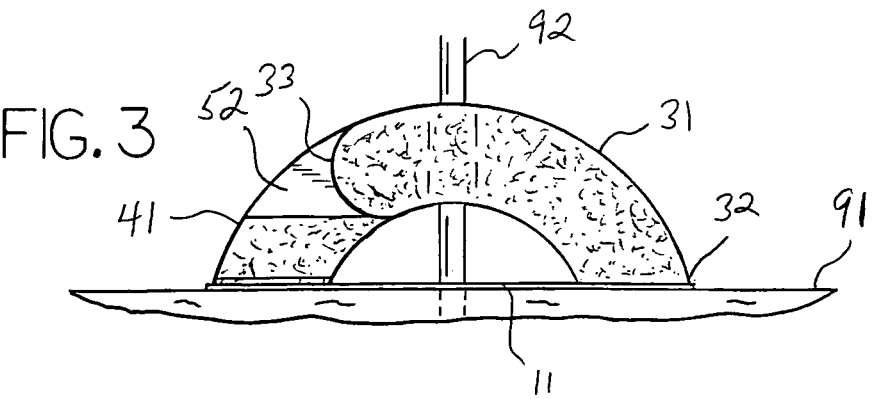
FIG. 3 is a rear view of the embodiment of FIG. 1 showing the bridging members joined to each other and securing a catheter.

With reference to the drawings, embodiments of the invention will now be described in detail with regard for the best mode and the preferred embodiment. In general, the invention is a catheter securement device adapted to secure and retain a percutaneously inserted catheter or similar medical line, wherein the catheter is oriented generally perpendicularly to the skin surface. The catheter securement device is adhesively attached to the skin of the patient and releasably secures the catheter. The catheter securement device is particularly suited for use with newborns having a catheter inserted into the umbilical stump, but the device is not limited to this application. The term catheter as used herein shall be taken as representing and encompassing any type of percutaneous medical line, such as for example a catheter, an intravenous (IV) tube, a drainage tube, etc. References herein to the upper direction and the lower direction shall refer to the direction away from the skin and the direction toward the skin, respectively. The drawings are illustrative in nature, and in particular the thickness dimension of the base member, securing member and various adhesive layers are not to scale, the adhesive layer thicknesses in certain figures being exaggerated relative to the thicknesses of the base and sheet members for clarity purposes.

The catheter securement device comprises a base member 11 selectively joined to a securing member 21, as best seen in FIG. 4. Both the base member 11 and the securing member 21 are composed of flexible sheet material, such that each is relatively thin in vertical cross-section. The base member 11 is adapted for adhesion to the skin 91 of a patient and may be composed for example of a medical grade adhesive bandage material, such as a polymer film provided with a layer of adhesive, or a self-adhering material such as a hydrocolloid patch, whereby the base member 11 can be applied to the skin 91, will remain adhered for a suitable time period, and then easily removed. The base member 11 comprises an upper surface 12, a lower surface 13, an internal edge 14 and an external edge 15. The base member 11 internal edge 14 defines an interior opening 61. A slot 62 extends from the interior opening 61 completely through and across the body of the base member 11. Preferably the internal edge 14 and the external edge 15 are circular in configuration as shown, such that the base member 11 is generally C-shaped and the interior opening 61 is generally circular. Alternatively, the general configuration could be oval, rectangular or any other configuration.

Preferably the configuration of the securing member 21 matches that of the base member 11, such that the securing member 21 is likewise generally C-shaped. The securing member 21 may be composed of a flexible material suitable for use in medical applications, such as a tape, polymer or fabric material, and must possess sufficient strength such that movement of the catheter 92 will be suitably restricted when the device is in use. The securing member 21 comprises an upper surface 22, a lower surface 23, an internal edge 24 and an external edge 25. The internal edge 24 of the securing member 21 also preferably defines the interior opening 61, and slot 62 extends from the interior opening 61 completely through and across the body of the securing member 21.

The base member 11 and securing member 21 are selectively joined in a co-planar relationship, the junction being non-coextensive. A mounting adhesive layer 51 is applied to opposing sides of the either the base member upper surface 12 or the securing member lower surface 23, preferably in the shape of a strip extending across the interior openings 16 and 26, such that a portion of the mounting adhesive layer 51 is on one side of the opening 61 and a portion of the mounting adhesive layer 51 is on the opposite side of the opening 61. The mounting adhesive layer 51 is preferably oriented at an angle of between about 20 to 60 degrees relative to the slot 62, with an angle of about 35 degrees being most preferable. The width of the mounting adhesive layer 51 is preferably sized such that it does not encompass the slot 62. Any adhesive material suitable for use in medical applications and capable of bonding the base member 11 and securing member 21 may be utilized. Alternatively, other joining methodologies such as heat bonding, stitching, etc. may be used.

In this manner the securing member 21 is divided into at least four defined segments, two of the segments being disposed on opposite sides of the interior opening 61 and being segments wherein the securing member 21 is joined to the base member 11, and two of the segments likewise disposed on opposite sides of the interior opening 61 and being segments that are not coextensively joined to the base member 11. These latter segments are a first bridging member 31 and a second bridging member 41. First bridging member 31 comprises an attached end 32 that operates in a hinge-like manner and a free end 33, with free end 33 abutting slot 62. Second bridging member 41 comprises a first attached end 42 and a second attached end 43, both of which operate in a hinge-like manner. With this structure, the first bridging member 31 is a flap-like member that is free to fold away and upward from the base member 11 toward the center of the catheter securement device. Likewise, the second bridging member 41 is a flap-like member that is free to fold away and upward from the base member 11 toward the center of the catheter securement device, as shown if FIGS. 5 and 6.

Figure 7:
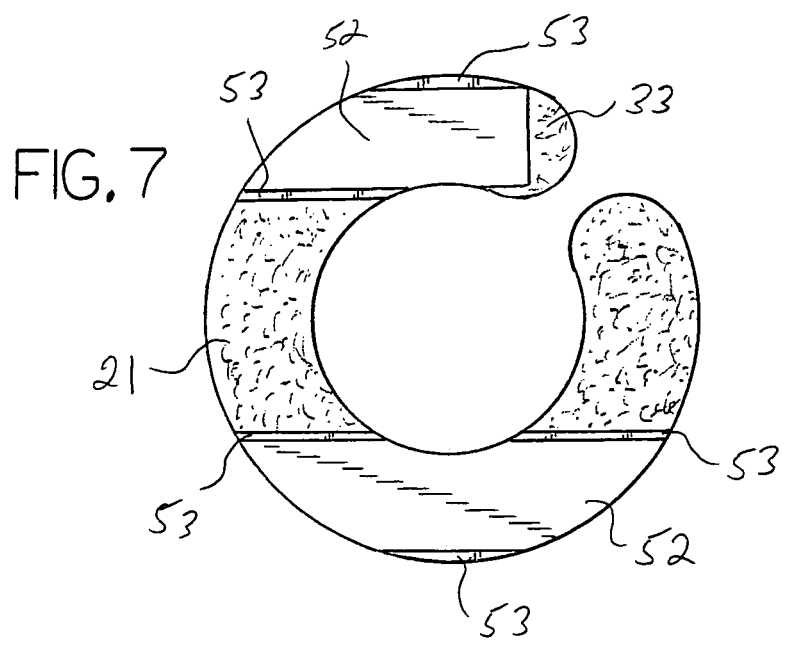
FIG. 7 is a top view of an alternative embodiment of the catheter securement device.

At least one of the upper surfaces 22 of the first and second bridging members 31 and 41, and preferably both of the upper surfaces 22, are provided with a securing adhesive layer 52 capable of joining the first and second bridging members 31 and 41 in a releasable manner with the catheter 92 secured therebetween. Any adhesive suitable for use in medical applications that possesses the requisite characteristics of being able to securely yet releasably join the two bridging members 31 can be utilized. Preferably, a silicone-based adhesive or silicone-compatible adhesive is utilized, since it is also desirable that the securing adhesive layer 52 also adhere to the catheter 92 itself. The adhesive layer 52 is not required to fully extend to the tip of the free end 33, as shown in FIG. 7. In certain embodiments, as also illustrated in FIG. 7, it may be necessary to provide a base adhesive layer 53 between the securing adhesive layer 52 and the bridging members 31 and 41, such as for example when a particular adhesive chosen for the securing adhesive layer 52 is not suitable for adhesion to the material of choice for the securing member 21.

Figure 6:
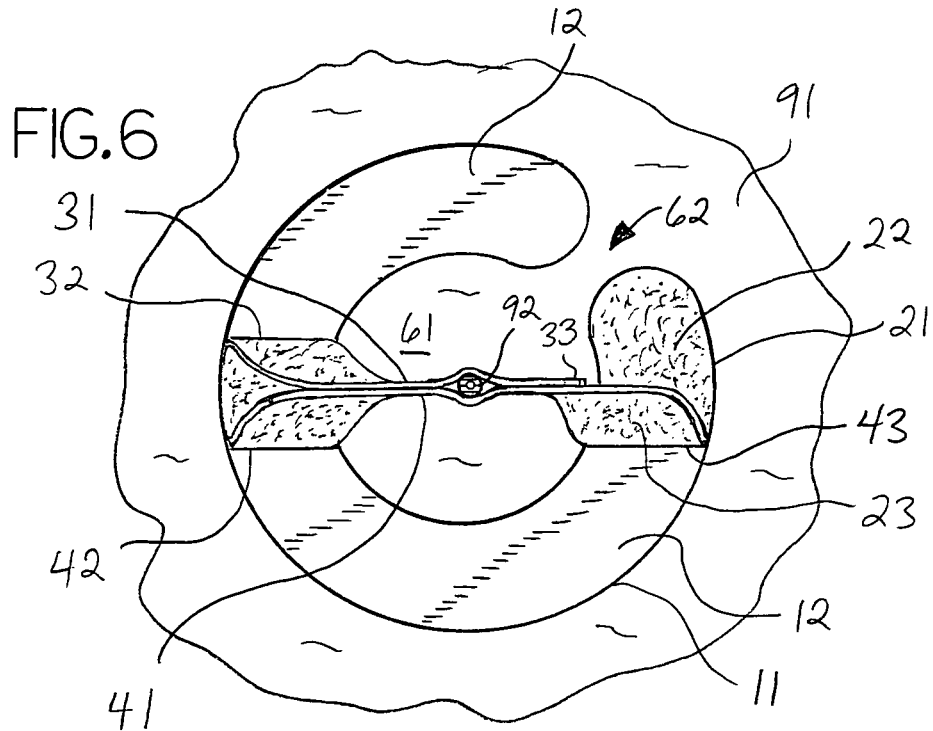
FIG. 6 is a top view of the embodiment of FIG. 1 showing the bridging members joined to each other and securing a catheter.

The catheter securement device is preferably packaged with a lower release liner member and an upper release liner member, as is well known in the art. With the catheter 92 properly inserted and any lower release liner member removed from the lower surface 13 of the base member 11, the catheter securement device is properly positioned on the patient encircling the catheter 92 by advancing the device such that catheter 92 passes through slot 62. The base member 11 is then adhered to the patient's skin 91 with the catheter 92 centered in the interior opening 61. The upper release liner member is then removed to expose the securing adhesive layer 52 on one or both of the bridging members 31 and 41. The bridging members 31 and 41 are then folded upward and together to secure the catheter 92 in between. As seen in FIG. 6, the combination of the first and second bridging members 31 and 41 creates a generally stiff securing bridge connected to the base member 11, the bridge having three legs formed by the attached end 32 of the first bridging member 31 and the first and second attached ends 42 and 43 of second bridging member 41. Free end 33 of first bridging member 31 by necessity extends past the catheter 92 a sufficient distance to be secured to the second bridging member 41, and further provides the means for separating the bridging members 31 and 41, since the free end 33 can be grasped to pull the first bridging member 31 from the second bridging member 41 to release the catheter 92.

For example only and with the express intention of not being limiting in any manner, an embodiment of the catheter securement of suitable size based on a circular configuration may have an external radius of approximately 22 mm and an internal radius defining the interior opening 61 of approximately 12 mm. The slot 62 may have a width of approximately 3 mm. the width of the mounting adhesive layer 51 may be approximately 8 mm and the width of the securing adhesive layer 52 on each bridging member 31 and 41 may be approximately 10 mm.

It is understood and contemplated that equivalents and substitutions for certain elements and structures set forth above may be obvious to one of ordinary skill in the art, and therefore the true scope and definition of the invention is to be as set forth in the following claims.

We claim:

1. A slotted catheter securement device adapted for securing a catheter extending generally perpendicularly from skin of a patient, said catheter having a diameter, the device comprising:

a base member and a generally C-shaped securing member each composed of a flexible sheet material, said securing member and said base member co-planarly oriented, said securing member joined to said base member non-coextensively;

an interior opening defined by said base member and said securing member;

a slot passing through said base member and said securing member in communication with said interior opening, said slot being of a greater width than the diameter of the catheter;

wherein said slot allows said catheter securement device to be positioned or removed with said catheter already in place on said patient;

said securing member comprising an elongated, curved first bridging member non-coextensively joined to said base member and an elongated, curved second bridging member non-coextensively joined to said base member, said first bridging member and said second bridging member having a curved internal edge and a curved external edge;

a securing adhesive layer positioned on at least one of said first and second bridging members;

said first bridging member having an attached end hingedly joined to said base member and a free end not joined to said base member and abutting said slot;

said second bridging member having two attached ends hingedly joined to said base member;

whereby said first and second bridging members fold away from said base member to adhere to each other and to said catheter disposed therebetween.

2. The device of claim 1, further comprising a mounting adhesive layer joining said base member and said securing member, said mounting adhesive layer positioned on opposite sides of said interior opening, said mounting adhesive layer not encompassing said slot.

3. The device of claim 2, wherein said base member is generally C-shaped.

4. The device of claim 1, wherein said base member is generally C-shaped.

5. The device of claim 1, wherein said securing adhesive layer is not positioned on said free end of said first bridging member.

6. The device of claim 1, wherein said base member comprises a hydrocolloid patch.

7. The device of claim 1, further comprising a base adhesive layer disposed between said securing adhesive layer and said securing member.

8. The device of claim 1, wherein said base member adheres to the skin of the patient.

9. The device of claim 1, wherein said base member, said securing member and said interior opening are generally circular in configuration.

10. A slotted catheter securement device adapted for securing a catheter extending generally perpendicularly from skin of a patient, the catheter having a diameter, the device comprising:

a base member composed of a flexible sheet material and adhesively adherable to the skin of the patient, said base member having an upper surface and a lower surface;

a generally C-shaped securing member composed of a flexible sheet material, said securing member having an upper surface and a lower surface; said lower surface of said securing member joined in a co-planar, non-coextensive manner to said upper surface of said base member;

a central interior opening defined by said base member and said securing member;

a slot passing through said base member and said securing member in communication with said interior opening, said slot being of a greater width than the diameter of the catheter;

wherein said slot allows said catheter securement device to be positioned or removed with said catheter already in place on said patient;

said securing member joined to said base member such that at least four segments are defined on said securing member, two of said segments being coextensively joined to said base member and the other two of said segments being not coextensively joined to said base member;

said two non-coextensively joined segments of said securing member defining respectively an elongated, curved first bridging member and an elongated, curved second bridging member, said first bridging member and said second bridging member having a curved internal edge and a curved external edge;

a securing adhesive layer positioned on said upper surface of said securing member on at least one of said first and second bridging members;

said first bridging member having an attached end hingedly joined to said base member and a free end not joined to said base member and abutting said slot;

said second bridging member having two attached ends hingedly joined to said base member;

whereby said first and second bridging members fold together away from said base member to adhere to each other and to the catheter disposed therebetween.

11. The device of claim 10, further comprising a mounting adhesive layer joining said upper surface of said base member to said lower surface of said securing member to define said two coextensively joined segments, said mounting adhesive layer positioned on opposite sides of said interior opening, and said mounting adhesive layer not encompassing said slot.

12. The device of claim 11, wherein said base member is generally C-shaped.

13. The device of claim 11, wherein said securing adhesive layer is not positioned on said free end of said first bridging member.

14. The device of claim 10, wherein said base member is generally C-shaped.

15. The device of claim 14, wherein said securing adhesive layer is not positioned on said free end of said first bridging member.

16. The device of claim 10, wherein said securing adhesive layer is not positioned on said free end of said first bridging member.

17. The device of claim 10, wherein said base member comprises a hydrocolloid patch.

18. The device of claim 10, further comprising a base adhesive layer disposed between said upper surface of said securing member and said securing adhesive layer.

19. The device of claim 10, wherein said base member adheres to the skin of the patient.

20. The device of claim 10, wherein said base member, said securing member and said interior opening are generally circular in configuration.

* * * * *

UNITED STATES PATENT AND TRADEMARK OFFICE
CERTIFICATE OF CORRECTION

| | | |
|---|---|---|
| PATENT NO. | : 8,834,427 B2 | |
| APPLICATION NO. | : 13/134498 | |
| DATED | : September 16, 2014 | |
| INVENTOR(S) | : Kurt Kyvik et al. | |

It is certified that error appears in the above-identified patent and that said Letters Patent is hereby corrected as shown below:

Title page

(75) Inventors should read: KURT KYVIK, OCALA, FL (US); ARTHUR PARKHURST, OCALA, FL (US)

Signed and Sealed this
Tenth Day of November, 2015

Michelle K. Lee
*Director of the United States Patent and Trademark Office*